US011484603B2

(12) United States Patent
Viswanathan et al.

(10) Patent No.: US 11,484,603 B2
(45) Date of Patent: Nov. 1, 2022

(54) METHODS, SYSTEMS, AND COMPOSITIONS FOR INHIBITING VIRULENCE OF A/E FAMILY PATHOGENS

(71) Applicant: ARIZONA BOARD OF REGENTS ON BEHALF OF THE UNIVERSITY OF ARIZONA, Tucson, AZ (US)

(72) Inventors: Virinchipuram K. Viswanathan, Tucson, AZ (US); Gayatri Vedantam, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 314 days.

(21) Appl. No.: 16/499,567

(22) PCT Filed: Mar. 30, 2018

(86) PCT No.: PCT/US2018/025408
§ 371 (c)(1),
(2) Date: Sep. 30, 2019

(87) PCT Pub. No.: WO2018/183850
PCT Pub. Date: Oct. 4, 2018

(65) Prior Publication Data
US 2021/0008221 A1    Jan. 14, 2021

Related U.S. Application Data

(60) Provisional application No. 62/479,596, filed on Mar. 31, 2017.

(51) Int. Cl.
A61K 47/64    (2017.01)
A61P 31/04    (2006.01)
C07K 14/245   (2006.01)

(52) U.S. Cl.
CPC .......... *A61K 47/6425* (2017.08); *A61P 31/04* (2018.01); *C07K 14/245* (2013.01)

(58) Field of Classification Search
None
See application file for complete search history.

(56) References Cited

U.S. PATENT DOCUMENTS

| 2010/0222261 A1 | 9/2010 | Bagnard et al. |
| 2010/0291596 A1 | 11/2010 | Multhaup et al. |
| 2016/0298078 A1 | 10/2016 | Guay et al. |

FOREIGN PATENT DOCUMENTS

| WO | 2007000672 A2 | 1/2007 |
| WO | 2009068269 A1 | 6/2009 |
| WO | 2010043046 A1 | 4/2010 |
| WO | 2015177197 A1 | 11/2015 |

OTHER PUBLICATIONS

Shoji-Kawata et al. (Identification of a candidate therapeutic autophagy inducing peptide Nature, Feb. 14, 2013; 494(7436); 201-206).*
Nataro JP et al., Diarrheagenic *Escherichia coli*, Clin Microbiol Rev, 1998, 11(1): 142-201.
Dean et al., Potent diarrheagenic mechanism mediated by the cooperative action of three enteropathogenic *Escherichia coli*-injected effector proteins, Proceedings of the National Academy of Sciences of the United States of America, 2006, 103(6), 1876-81.
Nguyen, Enterohemorrhagic *E. coli* (EHEC) pathogenesis, Front Cell Infect Microbiol, 2012, 2: 90.PMC3417627.
Santos et al., Bringing down the host: enteropathogenic and enterohaemorrhagic *Escherichia coli* effector-mediated subversion of host innate immune pathways, Cell Microbiol, 2015, 17(3): 318-32.
Wilbur et al., The secreted effector protein EspZ is essential for virulence of rabbit enteropathogenic *Escherichia coli*, Infect Immun, 2015, 83(3): 1139-49.PMC4333479.
Roxas et al., The enteropathogenic *Escherichia coli*-secreted protein EspZ inhibits host cell apoptosis, Infect Immun, 2012, 80(11): 3850-7.PMC3486051.
Roxas et al., Enteropathogenic *Escherichia coli* dynamically regulates EGFR signaling in intestinal epithelial cells, Am J Physiol Gastrointest Liver Physiol, 2014, 307(3): G374-80.PMC4121633.
Charpentier et al., Identification of the secretion and translocation domain of the enteropathogenic and enterohemorrhagic *Escherichia coli* effector Cif, using TEM-1 beta-lactamase as a new fluorescence-based reporter, Journal of Bacteriology, 2004, 186(16): 5486-95.
Bronnimann et al., A transmembrane domain and GxxxG motifs within L2 are essential for papillomavirus infection, J Virol, 2013, 87(1): 464-73.PMC3536380.
Pourahmad et al., Mitochondrial Targeting for Drug Development, Toxicology Studies—Cells, Drugs and Environment, Ana Cristina Andreazza and Gustavo Scola, IntechOpen, 2015, DOI: 10.5772/59719.
Carew et al., Mitochondrial defects in cancer, Mol Cancer 1, 9, 2002, doi:10.1186/1476-4598-1-9.
Smith et al., Mitochondrial Pharmacology, Trends in Pharmacological Sciences, Jun. 2012, vol. 33, No. 6.

(Continued)

*Primary Examiner* — Julie Ha
*Assistant Examiner* — Tara L Martinez
(74) *Attorney, Agent, or Firm* — Nguyen Tarbet LLC

(57) ABSTRACT

The present invention features methods, systems, and compositions for inhibiting function of EspZ or an EspZ equivalent, and for inhibiting or reducing virulence of pathogens that utilize EspZ or EspZ equivalent, such as those pathogens that belong to the attaching-effacing (A/E) family. The methods may feature the use of an inhibitor peptide that targets at least a portion of EspZ, such as one of the transmembrane domains. In certain embodiments, the inhibitor peptide disrupts proper dimerization or oligomerization of EspZ.

2 Claims, 4 Drawing Sheets
(4 of 4 Drawing Sheet(s) Filed in Color)
Specification includes a Sequence Listing.

(56) References Cited

OTHER PUBLICATIONS

Berger et al.. EspZ of enteropathogenic and enterohemorrhagic *E. coli* regulates type III secretion system protein translocation, mBio, 2012, 3(S):eOO317-12 doi:10,I128/mBio.OO317-12.

Creasey et al., Yeast two-hybrid system survey of interactions between LEE-encoded proteins of enteropathogenic *Escherichia coli,* Microbiology, Aug. 1, 2003, vol. 149, pp. 2093-2106.

Uniprot Submission Q47632 ECOLX, Nov. 1, 1996 [online]. [retrieved on Jul. 28, 2018], Retrieved from the internet <URL: http://www.uniprot.org/uniprot/Q47632>.

Invitation to Pay Additional Fees Issued For PCT Application No. PCT/US2018/025408 dated Jun. 18, 2018.

Beerens et al., Protein Transduction Domains and their Utility in Gene Therapy, Curr Gene Ther, 2003, 3(5):486-94.

Bitler et al., IntracellularMUC1Peptides Inhibit Cancer Progression, Clinical Cancer Research, 2009, 15:100-109.

Kotloff et al., Burden and aetiology of diarrhoeal disease in infants and young children in developing countries (the Global Enteric Multicenter Study, GEMS): a prospective, case-control study, Lancet, 2013, 382(9888), 209-22.

Hazen et al., Genomic diversity of EPEC associated with clinical presentations of differing severity, Nat Microbiol, 2016, 1: 15014. PMC5067155.

Teese et al., Role of GxxxG Motifs in Transmembrane Domain Interactions, Biochemistry, 2015, 54(33), 5125-35.

Dietz et al., Delivery of bioactive molecules into the cell: the Trojan horse approach, Molecular and Cellular Neuroscience, 2004, 27:85-131.

\* cited by examiner

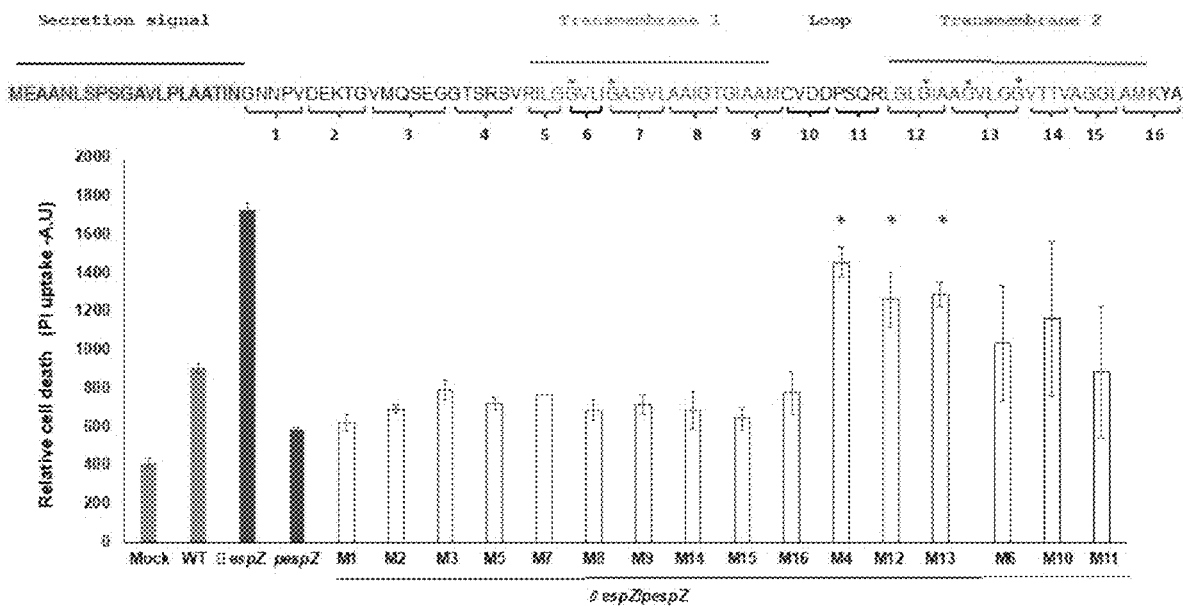

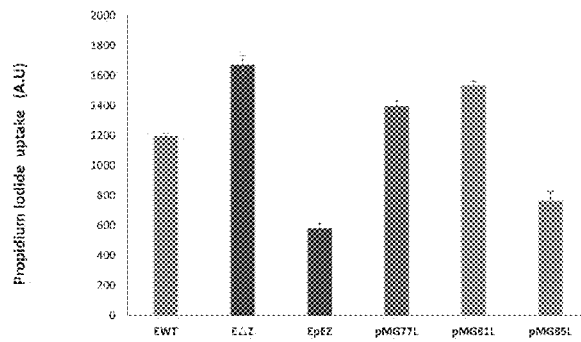
FIG. 3
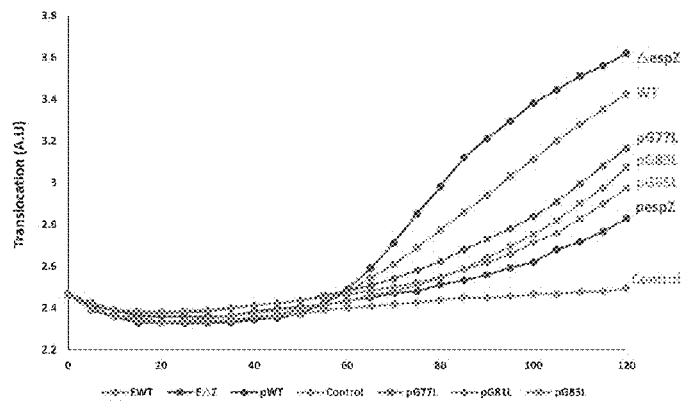
FIG. 4
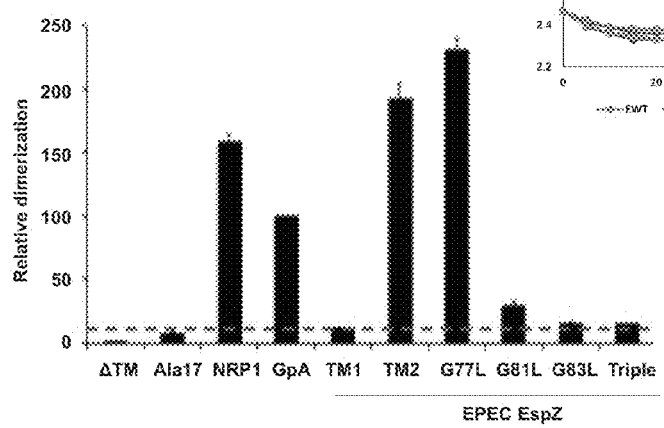
FIG. 5A
FIG. 5B
| EPEC EspZ | | SEQ ID NO: |
|---|---|---|
| TM1 | RILGGVLIGAGVLAAIGTGIAAM | 18 |
| TM2 | LGLGIAAGVLGGVTTVAGGLAMK | 19 |
| G77L | LGLLIAAGVLGGVTTVAGGLAMK | 20 |
| G81L | LGLGIAALVLGGVTTVAGGLAMK | 21 |
| G83L | LGLGIAAGVLGLVTTVAGGLAMK | 22 |
| Triple | LGLLIAALVLGLVTTVAGGLAMK | 23 |

SEQUENCE LISTING

```
<160> NUMBER OF SEQ ID NOS: 68

<210> SEQ ID NO 1
<211> LENGTH: 98
<212> TYPE: PRT
<213> ORGANISM: Escherichia coli

<400> SEQUENCE: 1

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Val Met
            20                  25                  30

Gln Ser Glu Gly Gly Thr Ser Arg Ser Val Arg Ile Leu Gly Gly Val
        35                  40                  45

Leu Ile Gly Ala Gly Val Leu Ala Ala Ile Gly Thr Gly Ile Ala Ala
    50                  55                  60

Met Cys Val Asp Asp Pro Ser Gln Arg Leu Gly Leu Gly Ile Ala Ala
65                  70                  75                  80

Gly Val Leu Gly Gly Val Thr Thr Val Ala Gly Gly Leu Ala Met Lys
                85                  90                  95

Tyr Ala

<210> SEQ ID NO 2
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 2

Met Glu Ala Ala Asn Leu Ser Pro Ser Gly Ala Val Leu Pro Leu Ala
1               5                   10                  15
```

```
Ala Thr Ile Asn Ala Ala Ala Ala Asp Glu Lys Thr Gly Val Met
            20                  25                  30

Gln Ser Glu Gly Gly Thr Ser Arg Ser Val Arg Ile Leu Gly Gly Val
        35                  40                  45

Leu Ile Gly Ala Gly Val Leu Ala Ala Ile Gly Thr Gly Ile Ala Ala
    50                  55                  60

Met Cys Val Asp Asp Pro Ser Gln Arg Leu Gly Leu Gly Ile Ala Ala
65                  70                  75                  80

Gly Val Leu Gly Gly Val Thr Thr Val Ala Gly Gly Leu Ala Met Lys
                85                  90                  95

Tyr Ala

<210> SEQ ID NO 3
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 3

Met Glu Ala Ala Asn Leu Ser Pro Ser Gly Ala Val Leu Pro Leu Ala
1               5                   10                  15

Ala Thr Ile Asn Gly Asn Asn Pro Val Ala Ala Ala Ala Val Met
            20                  25                  30

Gln Ser Glu Gly Gly Thr Ser Arg Ser Val Arg Ile Leu Gly Gly Val
        35                  40                  45

Leu Ile Gly Ala Gly Val Leu Ala Ala Ile Gly Thr Gly Ile Ala Ala
    50                  55                  60

Met Cys Val Asp Asp Pro Ser Gln Arg Leu Gly Leu Gly Ile Ala Ala
65                  70                  75                  80

Gly Val Leu Gly Gly Val Thr Thr Val Ala Gly Gly Leu Ala Met Lys
                85                  90                  95

Tyr Ala

<210> SEQ ID NO 4
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 4

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Ala Ala
            20                  25                  30

Ala Ala Ala Ala Gly Thr Ser Arg Ser Val Arg Ile Leu Gly Gly Val
        35                  40                  45

Leu Ile Gly Ala Gly Val Leu Ala Ala Ile Gly Thr Gly Ile Ala Ala
    50                  55                  60

Met Cys Val Asp Asp Pro Ser Gln Arg Leu Gly Leu Gly Ile Ala Ala
65                  70                  75                  80

Gly Val Leu Gly Gly Val Thr Thr Val Ala Gly Gly Leu Ala Met Lys
                85                  90                  95

Tyr Ala
```

-continued

<210> SEQ ID NO 5
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 5

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Val Met
            20                  25                  30

Gln Ser Glu Gly Ala Ala Ala Ala Ala Arg Ile Leu Gly Val
        35                  40                  45

Leu Ile Gly Ala Gly Val Leu Ala Ala Ile Gly Thr Gly Ile Ala Ala
    50                  55                  60

Met Cys Val Asp Asp Pro Ser Gln Arg Leu Gly Leu Gly Ile Ala Ala
65                  70                  75                  80

Gly Val Leu Gly Gly Val Thr Thr Val Ala Gly Leu Ala Met Lys
                85                  90                  95

Tyr Ala

<210> SEQ ID NO 6
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 6

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Val Met
            20                  25                  30

Gln Ser Glu Gly Gly Thr Ser Arg Ser Val Ala Ala Ala Gly Val
        35                  40                  45

Leu Ile Gly Ala Gly Val Leu Ala Ala Ile Gly Thr Gly Ile Ala Ala
    50                  55                  60

Met Cys Val Asp Asp Pro Ser Gln Arg Leu Gly Leu Gly Ile Ala Ala
65                  70                  75                  80

Gly Val Leu Gly Gly Val Thr Thr Val Ala Gly Leu Ala Met Lys
                85                  90                  95

Tyr Ala

<210> SEQ ID NO 7
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 7

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Val Met
            20                  25                  30

Gln Ser Glu Gly Gly Thr Ser Arg Ser Val Arg Ile Leu Ala Val Ala
        35                  40                  45

Ala Ala Gly Ala Gly Val Leu Ala Ile Gly Thr Gly Ile Ala Ala
            50                  55                  60

Met Cys Val Asp Asp Pro Ser Gln Arg Leu Gly Leu Gly Ile Ala Ala
 65                  70                  75                  80

Gly Val Leu Gly Gly Val Thr Thr Val Ala Gly Gly Leu Ala Met Lys
                85                  90                  95

Tyr Ala

<210> SEQ ID NO 8
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 8

Met Glu Ala Ala Asn Leu Ser Pro Ser Gly Ala Val Leu Pro Leu Ala
  1               5                  10                  15

Ala Thr Ile Asn Gly Asn Asn Pro Val Asp Glu Lys Thr Gly Val Met
             20                  25                  30

Gln Ser Glu Gly Gly Thr Ser Arg Ser Val Arg Ile Leu Gly Gly Val
         35                  40                  45

Leu Ile Val Ala Ala Ala Ala Ala Ile Gly Thr Gly Ile Ala Ala
     50                  55                  60

Met Cys Val Asp Asp Pro Ser Gln Arg Leu Gly Leu Gly Ile Ala Ala
 65                  70                  75                  80

Gly Val Leu Gly Gly Val Thr Thr Val Ala Gly Gly Leu Ala Met Lys
                85                  90                  95

Tyr Ala

<210> SEQ ID NO 9
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 9

Met Glu Ala Ala Asn Leu Ser Pro Ser Gly Ala Val Leu Pro Leu Ala
  1               5                  10                  15

Ala Thr Ile Asn Gly Asn Asn Pro Val Asp Glu Lys Thr Gly Val Met
             20                  25                  30

Gln Ser Glu Gly Gly Thr Ser Arg Ser Val Arg Ile Leu Gly Gly Val
         35                  40                  45

Leu Ile Gly Ala Gly Val Leu Ala Ala Ala Ala Gly Ile Ala Ala
     50                  55                  60

Met Cys Val Asp Asp Pro Ser Gln Arg Leu Gly Leu Gly Ile Ala Ala
 65                  70                  75                  80

Gly Val Leu Gly Gly Val Thr Thr Val Ala Gly Gly Leu Ala Met Lys
                85                  90                  95

Tyr Ala

<210> SEQ ID NO 10
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 10

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Val Met
            20                  25                  30

Gln Ser Glu Gly Gly Thr Ser Arg Ser Val Arg Ile Leu Gly Gly Val
        35                  40                  45

Leu Ile Gly Ala Gly Val Leu Ala Ala Ile Gly Thr Ala Ala Ala Ala
    50                  55                  60

Ala Cys Val Asp Asp Pro Ser Gln Arg Leu Gly Leu Gly Ile Ala Ala
65                  70                  75                  80

Gly Val Leu Gly Gly Val Thr Thr Val Ala Gly Gly Leu Ala Met Lys
                85                  90                  95

Tyr Ala

<210> SEQ ID NO 11
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 11

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Val Met
            20                  25                  30

Gln Ser Glu Gly Gly Thr Ser Arg Ser Val Arg Ile Leu Gly Gly Val
        35                  40                  45

Leu Ile Gly Ala Gly Val Leu Ala Ala Ile Gly Thr Gly Ile Ala Ala
    50                  55                  60

Met Ala Ala Ala Ala Pro Ser Gln Arg Leu Gly Leu Gly Ile Ala Ala
65                  70                  75                  80

Gly Val Leu Gly Gly Val Thr Thr Val Ala Gly Gly Leu Ala Met Lys
                85                  90                  95

Tyr Ala

<210> SEQ ID NO 12
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 12

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Val Met
            20                  25                  30

Gln Ser Glu Gly Gly Thr Ser Arg Ser Val Arg Ile Leu Gly Gly Val
        35                  40                  45

Leu Ile Gly Ala Gly Val Leu Ala Ala Ile Gly Thr Gly Ile Ala Ala
    50                  55                  60

Met Cys Val Asp Asp Ala Ala Ala Leu Gly Leu Gly Ile Ala Ala
65                  70                  75                  80

Gly Val Leu Gly Gly Val Thr Thr Val Ala Gly Gly Leu Ala Met Lys
                85                  90                  95

Tyr Ala

<210> SEQ ID NO 13
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 13

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Val Met
                20                  25                  30

Gln Ser Glu Gly Gly Thr Ser Arg Ser Val Arg Ile Leu Gly Val
            35                  40                  45

Leu Ile Gly Ala Gly Val Leu Ala Ala Ile Gly Thr Gly Ile Ala Ala
    50                  55                  60

Met Cys Val Asp Asp Pro Ser Gln Arg Ala Ala Ala Val Ala Ala Ala
65                  70                  75                  80

Gly Val Leu Gly Gly Val Thr Thr Val Ala Gly Gly Leu Ala Met Lys
                85                  90                  95

Tyr Ala

<210> SEQ ID NO 14
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 14

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Val Met
                20                  25                  30

Gln Ser Glu Gly Gly Thr Ser Arg Ser Val Arg Ile Leu Gly Val
            35                  40                  45

Leu Ile Gly Ala Gly Val Leu Ala Ala Ile Gly Thr Gly Ile Ala Ala
    50                  55                  60

Met Cys Val Asp Asp Pro Ser Gln Arg Leu Gly Leu Gly Ile Ala Ala
65                  70                  75                  80

Val Ala Ala Ala Val Val Thr Thr Val Ala Gly Gly Leu Ala Met Lys
                85                  90                  95

Tyr Ala

<210> SEQ ID NO 15
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 15

Met Glu Ala Ala Asn Leu Ser Pro Ser Gly Ala Val Leu Pro Leu Ala
1               5                   10                  15

```
Ala Thr Ile Asn Gly Asn Asn Pro Val Asp Glu Lys Thr Gly Val Met
            20                  25                  30

Gln Ser Glu Gly Gly Thr Ser Arg Ser Val Arg Ile Leu Gly Gly Val
        35                  40                  45

Leu Ile Gly Ala Gly Val Leu Ala Ala Ile Gly Thr Gly Ile Ala Ala
    50                  55                  60

Met Cys Val Asp Asp Pro Ser Gln Arg Leu Gly Leu Gly Ile Ala Ala
65                  70                  75                  80

Gly Val Leu Gly Gly Ala Ala Ala Ala Gly Gly Leu Ala Met Lys
                85                  90                  95

Tyr Ala

<210> SEQ ID NO 16
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 16

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Val Met
            20                  25                  30

Gln Ser Glu Gly Gly Thr Ser Arg Ser Val Arg Ile Leu Gly Gly Val
        35                  40                  45

Leu Ile Gly Ala Gly Val Leu Ala Ala Ile Gly Thr Gly Ile Ala Ala
    50                  55                  60

Met Cys Val Asp Asp Pro Ser Gln Arg Leu Gly Leu Gly Ile Ala Ala
65                  70                  75                  80

Gly Val Leu Gly Gly Val Thr Thr Val Ala Ala Ala Ala Met Lys
                85                  90                  95

Tyr Ala

<210> SEQ ID NO 17
<211> LENGTH: 98
<212> TYPE: PRT
<213> ORGANISM: Artificial Sequence
<220> FEATURE:
<223> OTHER INFORMATION: Mutant form of EspZ

<400> SEQUENCE: 17

Met Glu Ala Ala Asn Leu Ser Pro Ser Gly Ala Val Leu Pro Leu Ala
1               5                   10                  15

Ala Thr Ile Asn Gly Asn Asn Pro Val Asp Glu Lys Thr Gly Val Met
            20                  25                  30

Gln Ser Glu Gly Gly Thr Ser Arg Ser Val Arg Ile Leu Gly Gly Val
        35                  40                  45

Leu Ile Gly Ala Gly Val Leu Ala Ala Ile Gly Thr Gly Ile Ala Ala
    50                  55                  60

Met Cys Val Asp Asp Pro Ser Gln Arg Leu Gly Leu Gly Ile Ala Ala
65                  70                  75                  80

Gly Val Leu Gly Gly Val Thr Thr Val Ala Gly Leu Ala Ala Ala
                85                  90                  95

Ala Ala

<210> SEQ ID NO 18
```

```
<211> LENGTH: 23
<212> TYPE: PRT
<213> ORGANISM: Artificial Sequence
<220> FEATURE:
<223> OTHER INFORMATION: Transmembrane1 Region of EspZ

<400> SEQUENCE: 18

Arg Ile Leu Gly Gly Val Leu Ile Gly Ala Gly Val Leu Ala Ala Ile
1               5                   10                  15

Gly Thr Gly Ile Ala Ala Met
            20

<210> SEQ ID NO 19
<211> LENGTH: 23
<212> TYPE: PRT
<213> ORGANISM: Artificial Sequence
<220> FEATURE:
<223> OTHER INFORMATION: Transmembrane2 region of EspZ

<400> SEQUENCE: 19

Leu Gly Leu Gly Ile Ala Ala Gly Val Leu Gly Gly Val Thr Thr Val
1               5                   10                  15

Ala Gly Gly Leu Ala Met Lys
            20

<210> SEQ ID NO 20
<211> LENGTH: 23
<212> TYPE: PRT
<213> ORGANISM: Artificial Sequence
<220> FEATURE:
<223> OTHER INFORMATION: Artificial inhibitor peptide based on EspZ

<400> SEQUENCE: 20

Leu Gly Leu Leu Ile Ala Ala Gly Val Leu Gly Gly Val Thr Thr Val
1               5                   10                  15

Ala Gly Gly Leu Ala Met Lys
            20

<210> SEQ ID NO 21
<211> LENGTH: 23
<212> TYPE: PRT
<213> ORGANISM: Artificial Sequence
<220> FEATURE:
<223> OTHER INFORMATION: Artificial inhibitor peptide based on EspZ

<400> SEQUENCE: 21

Leu Gly Leu Gly Ile Ala Ala Leu Val Leu Gly Gly Val Thr Thr Val
1               5                   10                  15

Ala Gly Gly Leu Ala Met Lys
            20

<210> SEQ ID NO 22
<211> LENGTH: 23
<212> TYPE: PRT
<213> ORGANISM: Artificial Sequence
<220> FEATURE:
<223> OTHER INFORMATION: Artificial inhibitor peptide based on EspZ

<400> SEQUENCE: 22

Leu Gly Leu Gly Ile Ala Ala Gly Val Leu Gly Leu Val Thr Thr Val
1               5                   10                  15

Ala Gly Gly Leu Ala Met Lys
            20
```

<210> SEQ ID NO 23
<211> LENGTH: 23
<212> TYPE: PRT
<213> ORGANISM: Artificial Sequence
<220> FEATURE:
<223> OTHER INFORMATION: Artificial inhibitor peptide based on EspZ

<400> SEQUENCE: 23

Leu Gly Leu Leu Ile Ala Ala Leu Val Leu Gly Leu Val Thr Thr Val
1               5                   10                  15

Ala Gly Gly Leu Ala Met Lys
            20

<210> SEQ ID NO 24
<211> LENGTH: 13
<212> TYPE: PRT
<213> ORGANISM: Artificial Sequence
<220> FEATURE:
<223> OTHER INFORMATION: Cell-penetrating peptide (CPP)

<400> SEQUENCE: 24

Gly Arg Lys Lys Arg Arg Gln Arg Arg Arg Pro Pro Gln
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Cell-penetrating peptide (CPP)

<400> SEQUENCE: 25

Arg Lys Lys Arg Arg Gln Arg Arg Arg
1               5

<210> SEQ ID NO 26
<211> LENGTH: 9
<212> TYPE: PRT
<213> ORGANISM: Artificial Sequence
<220> FEATURE:
<223> OTHER INFORMATION: Cell-penetrating peptide (CPP)

<400> SEQUENCE: 26

Arg Lys Lys Arg Arg Gln Arg Arg Arg
1               5

<210> SEQ ID NO 27
<211> LENGTH: 19
<212> TYPE: PRT
<213> ORGANISM: Artificial Sequence
<220> FEATURE:
<223> OTHER INFORMATION: Cell-penetrating peptide (CPP)

<400> SEQUENCE: 27

Val Lys Arg Gly Leu Lys Leu Arg His Val Arg Pro Arg Val Thr Arg
1               5                   10                  15

Met Asp Val

<210> SEQ ID NO 28
<211> LENGTH: 27
<212> TYPE: PRT
<213> ORGANISM: Artificial Sequence
<220> FEATURE:
<223> OTHER INFORMATION: Cell-penetrating peptide (CPP)

<400> SEQUENCE: 28

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 29
<211> LENGTH: 21
<212> TYPE: PRT
<213> ORGANISM: Artificial Sequence
<220> FEATURE:
<223> OTHER INFORMATION: Cell-penetrating peptide (CPP)

<400> SEQUENCE: 29

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 30
<211> LENGTH: 18
<212> TYPE: PRT
<213> ORGANISM: Artificial Sequence
<220> FEATURE:
<223> OTHER INFORMATION: Cell-penetrating peptide (CPP)

<400> SEQUENCE: 30

Leu Leu Ile Ile Leu Arg Arg Arg Ile Arg Lys Gln Ala His Ala His
1               5                   10                  15

Ser Lys

<210> SEQ ID NO 31
<211> LENGTH: 22
<212> TYPE: PRT
<213> ORGANISM: Artificial Sequence
<220> FEATURE:
<223> OTHER INFORMATION: Cell-penetrating peptide (CPP)

<400> SEQUENCE: 31

Met Val Arg Arg Phe Leu Val Thr Leu Arg Ile Arg Arg Ala Cys Gly
1               5                   10                  15

Pro Pro Arg Val Arg Val
            20

<210> SEQ ID NO 32
<211> LENGTH: 28
<212> TYPE: PRT
<213> ORGANISM: Artificial Sequence
<220> FEATURE:
<223> OTHER INFORMATION: Cell-penetrating peptide (CPP)

<400> SEQUENCE: 32

Met Val Lys Ser Lys Ile Gly Ser Trp Ile Leu Val Leu Phe Val Ala
1               5                   10                  15

Met Trp Ser Asp Val Gly Leu Cys Lys Lys Arg Pro
            20                  25

<210> SEQ ID NO 33
<211> LENGTH: 18
<212> TYPE: PRT
<213> ORGANISM: Artificial Sequence
<220> FEATURE:
<223> OTHER INFORMATION: Cell-penetrating peptide (CPP)

<400> SEQUENCE: 33

Lys Leu Ala Leu Lys Leu Ala Leu Lys Ala Leu Lys Ala Ala Leu Lys
1               5                   10                  15

Leu Ala

<210> SEQ ID NO 34
<211> LENGTH: 27
<212> TYPE: PRT
<213> ORGANISM: Artificial Sequence
<220> FEATURE:
<223> OTHER INFORMATION: Cell-penetrating peptide (CPP)

<400> SEQUENCE: 34

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 35
<211> LENGTH: 28
<212> TYPE: PRT
<213> ORGANISM: Artificial Sequence
<220> FEATURE:
<223> OTHER INFORMATION: Cell-penetrating peptide (CPP)

<400> SEQUENCE: 35

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 36
<211> LENGTH: 28
<212> TYPE: PRT
<213> ORGANISM: Artificial Sequence
<220> FEATURE:
<223> OTHER INFORMATION: Cell-penetrating peptide (CPP)

<400> SEQUENCE: 36

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 37
<211> LENGTH: 24
<212> TYPE: PRT
<213> ORGANISM: Artificial Sequence
<220> FEATURE:
<223> OTHER INFORMATION: Cell-penetrating peptide (CPP)

<400> SEQUENCE: 37

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 38
<211> LENGTH: 17
<212> TYPE: PRT
<213> ORGANISM: Artificial Sequence
<220> FEATURE:
<223> OTHER INFORMATION: Cell-penetrating peptide (CPP)

-continued

```
<400> SEQUENCE: 38

Cys Ser Ile Pro Pro Glu Val Lys Phe Asn Lys Pro Phe Val Tyr Leu
1               5                   10                  15

Ile

<210> SEQ ID NO 39
<211> LENGTH: 15
<212> TYPE: PRT
<213> ORGANISM: Artificial Sequence
<220> FEATURE:
<223> OTHER INFORMATION: Cell-penetrating peptide (CPP)

<400> SEQUENCE: 39

Ser Asp Leu Trp Glu Met Met Met Val Ser Leu Ala Cys Gln Tyr
1               5                   10                  15

<210> SEQ ID NO 40
<211> LENGTH: 11
<212> TYPE: PRT
<213> ORGANISM: Artificial Sequence
<220> FEATURE:
<223> OTHER INFORMATION: Cell-penetrating peptide (CPP)

<400> SEQUENCE: 40

Tyr Ala Arg Ala Ala Ala Arg Gln Ala Arg Ala
1               5                   10

<210> SEQ ID NO 41
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 41

Leu Gly Leu Leu Ile Ala Ala Gly Val Leu Gly Gly Val Thr Thr Val
1               5                   10                  15

Ala Gly

<210> SEQ ID NO 42
<211> LENGTH: 14
<212> TYPE: PRT
<213> ORGANISM: Artificial Sequence
<220> FEATURE:
<223> OTHER INFORMATION: Artificial inhibitor peptide based on EspZ

<400> SEQUENCE: 42

Leu Gly Leu Leu Ile Ala Ala Gly Val Leu Gly Gly Val Thr
1               5                   10

<210> SEQ ID NO 43
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 43

Leu Gly Leu Leu Ile Ala Ala Gly Val Ile Gly Gly Val Thr Thr Val
1               5                   10                  15

Ala Gly

<210> SEQ ID NO 44
```

```
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 44

Leu Gly Leu Leu Phe Ala Ala Gly Val Leu Gly Gly Val Thr Thr Val
1               5                   10                  15

Ala Gly

<210> SEQ ID NO 45
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 45

Leu Gly Leu Leu Ile Ala Ala Gly Val Leu Gly Gly Val Ser Thr Val
1               5                   10                  15

Ala Gly

<210> SEQ ID NO 46
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 46

Leu Gly Leu Leu Ile Ala Ala Gly Val Leu Gly Phe Val Thr Thr Val
1               5                   10                  15

Ala Gly

<210> SEQ ID NO 47
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 47

Leu Gly Leu Leu Ile Ala Ala Gly Leu Leu Gly Gly Val Thr Thr Val
1               5                   10                  15

Ala Gly

<210> SEQ ID NO 48
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 48

Leu Gly Leu Gly Ile Ala Ala Leu Val Leu Gly Gly Val Thr Thr Val
1               5                   10                  15

Ala Gly

<210> SEQ ID NO 49
<211> LENGTH: 14
<212> TYPE: PRT
<213> ORGANISM: Artificial Sequence
<220> FEATURE:
```

<223> OTHER INFORMATION: Artificial inhibitor peptide based on EspZ

<400> SEQUENCE: 49

Leu Gly Leu Gly Ile Ala Ala Leu Val Leu Gly Gly Val Thr
1               5                   10

<210> SEQ ID NO 50
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 50

Leu Gly Leu Gly Ile Ala Ala Leu Val Leu Asn Gly Val Thr Thr Val
1               5                   10                  15

Ala Gly

<210> SEQ ID NO 51
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 51

Leu Gly Leu Gly Ile Ala Ala Leu Val Leu Ala Gly Val Thr Thr Val
1               5                   10                  15

Ala Gly

<210> SEQ ID NO 52
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 52

Leu Gly Leu Gly Ile Ala Ala Leu Val Leu Gly Gly Val Ser Thr Val
1               5                   10                  15

Ala Gly

<210> SEQ ID NO 53
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 53

Leu Gly Leu Gly Ile Ala Ala Leu Val Leu Gly Gly Val Thr Thr Leu
1               5                   10                  15

Ala Gly

<210> SEQ ID NO 54
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 54

Leu Gly Leu Gly Ile Ala Ala Leu Leu Leu Gly Gly Val Thr Thr Val
1               5                   10                  15

Ala Gly

<210> SEQ ID NO 55
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 55

Leu Gly Leu Gly Ile Ala Ala Gly Val Leu Gly Leu Val Thr Thr Val
1               5                   10                  15

Ala Gly

<210> SEQ ID NO 56
<211> LENGTH: 14
<212> TYPE: PRT
<213> ORGANISM: Artificial Sequence
<220> FEATURE:
<223> OTHER INFORMATION: Artificial inhibitor peptide based on EspZ

<400> SEQUENCE: 56

Leu Gly Leu Gly Ile Ala Ala Gly Val Leu Gly Leu Val Thr
1               5                   10

<210> SEQ ID NO 57
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 57

Leu Gly Leu Gly Ile Ala Ala Gly Val Leu Gly Leu Val Thr Thr Leu
1               5                   10                  15

Ala Gly

<210> SEQ ID NO 58
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 58

Leu Gly Leu Gly Ile Ala Ala Gly Val Leu Pro Leu Val Thr Thr Val
1               5                   10                  15

Ala Gly

<210> SEQ ID NO 59
<211> LENGTH: 18
<212> TYPE: PRT
<213> ORGANISM: Artificial Sequence
<220> FEATURE:
<223> OTHER INFORMATION: Artificial inhibitor peptide based on EspZ -continued

<400> SEQUENCE: 59

Leu Gly Leu Gly Ile Ala Ala Ala Val Leu Gly Leu Val Thr Thr Val
1               5                   10                  15

Ala Gly

<210> SEQ ID NO 60
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 60

Leu Gly Leu Gly Ile Ala Ala Gly Val Leu Gly Leu Leu Thr Thr Val
1               5                   10                  15

Ala Gly

<210> SEQ ID NO 61
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 61

Leu Gly Leu Gly Ile Ala Ala Gly Val Leu Gly Leu Val Thr Ser Val
1               5                   10                  15

Ala Gly

<210> SEQ ID NO 62
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 62

Leu Gly Leu Leu Ile Ala Ala Leu Val Leu Gly Leu Val Thr Thr Val
1               5                   10                  15

Ala Gly

<210> SEQ ID NO 63
<211> LENGTH: 14
<212> TYPE: PRT
<213> ORGANISM: Artificial Sequence
<220> FEATURE:
<223> OTHER INFORMATION: Artificial inhibitor peptide based on EspZ

<400> SEQUENCE: 63

Leu Gly Leu Leu Ile Ala Ala Leu Val Leu Gly Leu Val Thr
1               5                   10

<210> SEQ ID NO 64
<211> LENGTH: 18
<212> TYPE: PRT
<213> ORGANISM: Artificial Sequence
<220> FEATURE:
<223> OTHER INFORMATION: Artificial inhibitor peptide based on EspZ

```
<400> SEQUENCE: 64

Leu Gly Leu Leu Ile Ala Ala Leu Val Leu Gly Leu Val Thr Thr Leu
1               5                   10                  15

Ala Gly

<210> SEQ ID NO 65
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 65

Leu Gly Leu Leu Ile Ala Ala Leu Val Leu Pro Leu Val Thr Thr Val
1               5                   10                  15

Ala Gly

<210> SEQ ID NO 66
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 66

Leu Gly Leu Leu Ile Ala Ala Leu Val Leu Ala Leu Val Thr Thr Val
1               5                   10                  15

Ala Gly

<210> SEQ ID NO 67
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 67

Leu Gly Leu Leu Ile Ala Ala Leu Val Leu Gly Leu Leu Thr Thr Val
1               5                   10                  15

Ala Gly

<210> SEQ ID NO 68
<211> LENGTH: 18
<212> TYPE: PRT
<213> ORGANISM: Artificial Sequence
<220> FEATURE:
<223> OTHER INFORMATION: Artificial inhibitor peptide based on EspZ

<400> SEQUENCE: 68

Leu Gly Leu Leu Ile Ala Ala Leu Val Leu Gly Leu Val Ser Thr Val
1               5                   10                  15

Ala Gly
```

METHODS, SYSTEMS, AND COMPOSITIONS FOR INHIBITING VIRULENCE OF A/E FAMILY PATHOGENS

CROSS REFERENCE

This application is a 371 and claims benefit of PCT/US18/25408 filed Mar. 30, 2018, which claims benefit of U.S. Patent Application No. 62/479,596, filed Mar. 31, 2017, the specification(s) of which is/are incorporated herein in their entirety by reference.

GOVERNMENT SUPPORT

This invention was made with government support under Grant No. R01-AI081742 awarded by NIH. The government has certain rights in the invention.

REFERENCE TO SEQUENCE LISTING

Applicant asserts that the paper copy of the Sequence Listing is identical to the Sequence Listing in computer readable form found on the accompanying computer file, entitled >>>UNIA_17_18_PCT_ST25.txt<<<. The content of the sequence listing is incorporated herein by reference in its entirety.

FIELD OF THE INVENTION

The present invention relates to inhibiting virulence of pathogenic bacteria, for example bacteria belonging to the attaching and effacing (A/E) family, for example Enteropathogenic *Escherichia coli* (EPEC).

BACKGROUND OF THE INVENTION

Enteropathogenic *Escherichia coli* (EPEC) is a leading cause of diarrheal disease, particularly in developing countries. EPEC belongs to the attaching and effacing (A/E) family of pathogens, which all harbor a type III secretion system (T3SS) that delivers virulence proteins directly into host epithelial cells. These proteins mediate diverse structural and functional alterations that likely facilitate pathogenesis. EspZ, a ~100 amino acid secreted protein unique to NE pathogens, delays the death of EPEC-infected intestinal epithelial cells by inhibiting intrinsic apoptosis. This facilitates initial bacterial colonization. The sequence of EspZ is as follows: MEAANLSPSGAVLPLAATIN GNNPVDEKTG VMQSEGGTSR SVRILGGVLI GAGVLAAIGT GIAAMCVDDP SQRLGLGIAAG VLGGVTTVAG GLAMKYA (SEQ ID NO: 1).

The first ~20 amino acids of EspZ are believed to be required for secretion via the T3SS, and the protein includes two ~23 amino acid predicted transmembrane regions (TM1 and TM2) separated by a 8-10 amino acid loop region. As discussed herein, Inventors have surprisingly discovered that amino acids (aa) 37-42 and aa75-85 are important for EPEC EspZ function.

The present invention features methods, systems, and compositions (e.g., inhibitor peptides) for inhibiting EspZ function and/or downstream effects (e.g., for inhibiting dimerization of EspZ, etc.) or an EspZ equivalent. The methods, systems, and compositions may help reduce virulence of pathogens that utilize EspZ or EspZ equivalent (e.g., reduce the ability for the bacteria to colonize), such as those pathogens that belong to the A/E family. In certain embodiments, the methods feature targeting a first region (e.g., a first susceptibility region) and/or a second region (e.g., a second susceptibility region) of the EspZ or EspZ equivalent protein, such as but not limited to the amino acids (aa) 37-42 and/or aa75-85 of EspZ, or a portion of the amino acids thereof. Note the present invention also includes other bacteria including but not limited to *Citrobacter rodentium*, EPEC and EHEC, and emergent human pathogens that acquire the pathogenicity island in EPEC or EHEC.

SUMMARY OF THE INVENTION

The present invention features inhibitor peptides for inhibiting EspZ, for inactivating EspZ, for disrupting normal function of EspZ, for disrupting EspZ activity, for inhibiting dimerization of EspZ, for inhibiting oligomerization of EspZ, for inhibiting EspZ self-association in the membrane, etc. Inhibitor peptides may comprise a targeting peptide, wherein the targeting peptide binds to or interacts with at least a portion of EspZ, and a cell penetrating peptide (CPP) linked directly or indirectly to the targeting peptide. The CPP is for enhancing penetration of the targeting peptide into a cell. The inhibitor peptide disrupts EspZ activity. As used herein, the term "disrupts [disrupting, etc.] EspZ activity" may include but is not limited to reducing or inhibiting proper function of EspZ, reducing or inhibiting downstream events (e.g., signaling events) normally activated by EspZ function, reducing or inhibiting dimerization or oligomerization of EspZ, for inhibiting or reducing EspZ self-association in the membrane, etc.

In some embodiments, the targeting peptide of the inhibitor peptide binds to or interacts with one or more amino acids in aa37-42 of EspZ. In some embodiments, the targeting peptide binds to or interacts with one or more amino acids of aa38-43 of EspZ. In some embodiments, the targeting peptide binds to or interacts with one or more amino acids of aa39-44 of EspZ. In some embodiments, the targeting peptide binds to or interacts with one or more amino acids of aa40-45 of EspZ. In some embodiments, the targeting peptide binds to or interacts with one or more amino acids of aa41-46 of EspZ. In some embodiments, the targeting peptide binds to or interacts with one or more amino acids of aa42-48 of EspZ. In some embodiments, the targeting peptide binds to or interacts with one or more amino acids of aa45-60 of EspZ. In some embodiments, the targeting peptide binds to or interacts with one or more amino acids of aa75-85 of EspZ. In some embodiments, the targeting peptide binds to or interacts with one or more amino acids of aa70-85 of EspZ. In some embodiments, the targeting peptide binds to or interacts with one or more amino acids of aa70-90 of EspZ. In some embodiments, the targeting peptide binds to or interacts with one or more amino acids of aa65-85 of EspZ. In some embodiments, the targeting peptide binds to or interacts with one or more amino acids of aa65-90 of EspZ. In some embodiments, the targeting peptide binds to or interacts with one or more amino acids of aa75-97 of EspZ. In some embodiments, the targeting peptide binds to or interacts with at least a portion amino acids aa47-96 of EspZ associated with TM2 of EspZ.

In some embodiments, the inhibitor peptide comprises a peptide from 5 to 15 amino acids that is at least 90% identical to a set of consecutive amino acids of the EspZ sequence of identical length. In some embodiments, the inhibitor peptide comprises a peptide from 8 to 20 amino acids that is at least 90% identical to a set of consecutive amino acids of the EspZ sequence of identical length. In some embodiments, the inhibitor peptide comprises a peptide from 10 to 20 amino acids that is at least 90% identical to a set of consecutive amino acids of the EspZ sequence of identical length. In some embodiments, the inhibitor peptide comprises a peptide from 10 to 25 amino acids that is at least 90% identical to a set of consecutive amino acids of the EspZ sequence of identical length. In some embodiments, the inhibitor peptide comprises a peptide from 10 to 30 amino acids that is at least 90% identical to a set of consecutive amino acids of the EspZ sequence of identical length.

In some embodiments, the inhibitor peptide comprises a peptide from 5 to 15 amino acids that is at least 80% identical to a set of consecutive amino acids of the EspZ sequence of identical length. In some embodiments, the inhibitor peptide comprises a peptide from 2 to 20 amino acids that is at least 80% identical to a set of consecutive amino acids of the EspZ sequence of identical length. In some embodiments, the inhibitor peptide comprises a peptide from 10 to 20 amino acids that is at least 80% identical to a set of consecutive amino acids of the EspZ sequence of identical length. In some embodiments, the inhibitor peptide comprises a peptide from 10 to 25 amino acids that is at least 80% identical to a set of consecutive amino acids of the EspZ sequence of identical length. In some embodiments, the inhibitor peptide comprises a peptide from 10 to 30 amino acids that is at least 80% identical to a set of consecutive amino acids of the EspZ sequence of identical length.

In some embodiments, the inhibitor peptide comprises a peptide from 10 to 20 amino acids that is at least 70% identical to a set of consecutive amino acids of the EspZ sequence of identical length. In some embodiments, the inhibitor peptide comprises a peptide from 20 to 30 amino acids that is at least 70% identical to a set of consecutive amino acids of the EspZ sequence of identical length. In some embodiments, the inhibitor peptide comprises a peptide from 30 to 40 amino acids that is at least 70% identical to a set of consecutive amino acids of the EspZ sequence of identical length. In some embodiments, the inhibitor peptide comprises a peptide from 15 to 40 amino acids that is at least 70% identical to a set of consecutive amino acids of the EspZ sequence of identical length. In some embodiments, the inhibitor peptide comprises a peptide from 25 to 40 amino acids that is at least 70% identical to a set of consecutive amino acids of the EspZ sequence of identical length. In some embodiments, the inhibitor peptide comprises a peptide from 15 to 50 amino acids that is at least 70% identical to a set of consecutive amino acids of the EspZ sequence of identical length.

In some embodiments, the targeting peptide comprises one of SEQ ID NO: 20-23, SEQ ID NO: 41-68. In some embodiments, the targeting peptide comprises a peptide that is at least 99% identical to one of SEQ ID NO: 20-23, SEQ ID NO: 41-68. In some embodiments, the targeting peptide comprises a peptide that is at least 98% identical to one of SEQ ID NO: 20-23, SEQ ID NO: 41-68. In some embodiments, the targeting peptide comprises a peptide that is at least 97% identical to one of SEQ ID NO: 20-23, SEQ ID NO: 41-68. In some embodiments, the targeting peptide comprises a peptide that is at least 96% identical to one of SEQ ID NO: 20-23, SEQ ID NO: 41-68. In some embodiments, the targeting peptide comprises a peptide that is at least 95% identical to one of SEQ ID NO: 20-23, SEQ ID NO: 41-68. In some embodiments, the targeting peptide comprises a peptide that is at least 94% identical to one of SEQ ID NO: 20-23, SEQ ID NO: 41-68. In some embodiments, the targeting peptide comprises a peptide that is at least 93% identical to one of SEQ ID NO: 20-23, SEQ ID NO: 41-68. In some embodiments, the targeting peptide comprises a peptide that is at least 92% identical to one of SEQ ID NO: 20-23, SEQ ID NO: 41-68. In some embodiments, the targeting peptide comprises a peptide that is at least 91% identical to one of SEQ ID NO: 20-23, SEQ ID NO: 41-68. In some embodiments, the targeting peptide comprises a peptide that is at least 90% identical to one of SEQ ID NO: 20-23, SEQ ID NO: 41-68. In some embodiments, the targeting peptide comprises a peptide that is at least 85% identical to one of SEQ ID NO: 20-23, SEQ ID NO: 41-68. In some embodiments, the targeting peptide comprises a peptide that is at least 80% identical to one of SEQ ID NO: 20-23, SEQ ID NO: 41-68. In some embodiments, the targeting peptide comprises a peptide that is at least 75% identical to one of SEQ ID NO: 20-23, SEQ ID NO: 41-68.In some embodiments, the targeting peptide comprises a peptide that is at least 70% identical to one of SEQ ID NO: 20-23, SEQ ID NO: 41-68. In some embodiments, the targeting peptide comprises a peptide that is at least 65% identical to one of SEQ ID NO: 20-23, SEQ ID NO: 41-68. In some embodiments, the targeting peptide comprises a peptide that is at least 60% identical to one of SEQ ID NO: 20-23, SEQ ID NO: 41-68. In some embodiments, the targeting peptide comprises a peptide that is at least 55% identical to one of SEQ ID NO: 20-23, SEQ ID NO: 41-68.In some embodiments, the targeting peptide comprises a peptide that is at least 50% identical to one of SEQ ID NO: 20-23, SEQ ID NO: 41-68.

In some embodiments, the targeting peptide inhibits or reduces dimerization or oligomerization of EspZ. In some embodiments, the targeting peptide is from 10 to 30 amino acids in length.

In some embodiments, the CPP is HIV-1 Tat$_{48-60}$, HIV-1 Tat$_{49-57}$, Penetratin, Polyarginine, DPV1047, MPG, Pep-1, pVEC, ARF(1-22), BPrPr(1-28), MAP, Transportan, p28, VT5, Bac 7, C105Y, PFVYLI, Pep-7, or PTD-4.

The present invention also features methods of inhibiting or reducing virulence of a pathogen of the attaching-effacing (NE) family (e.g., *E. coil*). In certain embodiments, the method comprises introducing to the pathogen an inhibitor peptide according to the present invention (e.g., any embodiment described herein), wherein the inhibitor peptide disrupts EspZ function to inhibit or reduce virulence of the pathogen.

The present invention also features methods of inhibiting or reducing colonization of a pathogen of the attaching-effacing (NE) family (e.g., *E. coli*). In certain embodiments, the method comprises introducing to the pathogen an inhibitor peptide according to the present invention (e.g., any embodiment described herein), wherein the inhibitor peptide disrupts EspZ function to inhibit or reduce colonization of the pathogen.

The present invention also features methods of treating a subject infected with a pathogen in the attaching-effacing (NE) family (e.g., *E. coli*). In certain embodiments, the method comprises introducing to the subject an inhibitor peptide according to the present invention (e.g., any embodiment described herein), wherein the inhibitor peptide disrupts EspZ function to inhibit or reduce virulence of the pathogen.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the office upon request and payment of the necessary fee. The features and advantages of the present invention will become apparent from a consideration of the following detailed description presented in connection with the accompanying drawings in which:

FIG. 1 shows examples of targeted mutations introduced into pSR6 to systematically replace ~5 amino acid segments with alanine residues (except in M6, M7, M12, and M13, where the glycine residues were replaced with valine residues). Mutant 1 is SEQ ID NO: 2, Mutant 2 is SEQ ID NO: 3, Mutant 3 is SEQ ID NO: 4, Mutant 4 is SEQ ID NO: 5. Mutant 5 is SEQ ID NO: 6, Mutant 6 is SEQ ID NO: 7, Mutant 7 is SEQ ID NO: 8, Mutant 8 is SEQ ID NO: 9, Mutant 9 is SEQ ID NO: 10, Mutant 10 is SEQ ID NO: 11, Mutant 11 is SEQ ID NO: 12, Mutant 12 is SEQ ID NO: 13, Mutant 13 is SEQ ID NO: 14, Mutant 14 is SEQ ID NO: 15, Mutant 15 is SEQ ID NO: 16, and Mutant 16 is SEQ ID NO: 17.

FIG. 2 shows relative cell death of ΔespZ cells transformed with the various mutants in FIG. 1 (propidium iodide uptake assays). Ten mutant constructs showed minimal defects in complementation relative to pSR6 for curtaining host cell death, while three mutants (M6, M10, and M11) were modestly impaired for this phenotype. Three mutants, M4, M12, and M13, were significantly defective in their ability to complement ΔespZ.

FIG. 3 shows propidium iodide uptake assays for monitoring cell death of EPEC ΔespZ cells transformed with constructs with EspZ mutants (mutants with G residues in the EspZ glycine zipper motif replaced with leucine residues: pMG77L, pMG81L, and pMG85L). The alteration of the first to G residues of the glycine zipper (G77L and G81L) resulted in a failure to complement EPEC ΔespZ. Mutation of the third G residue had minimal impact on EspZ function. This helps show that sequences within the glycine zipper may be essential for the cytoprotective effects of EspZ on infected host cells.

FIG. 4 shows a TEM-1 β-lactamase reporter system assay for monitoring effector translocation into infected cells. Compared to uninfected cells, WT EPEC infection resulted in a progressive increase in the TEM-1 β-lactamase-dependent breakdown (detected by fluorescent shift) of the substrate CCF2. ΔespZ infection resulted in significantly greater effector translocation, and this was reversed by low-copy plasmid complementation, consistent with a role for EspZ in limiting effector translocation. Site-specific alteration of the three G residues in the glycine zipper motif variably impacted the rheostat function of EspZ; G to L mutation of the last G residue (G85) had minimal impact on rheostat function, while alteration of the first and second G residues (G77 and G83) partially impaired function.

FIG. 5A shows a ToxLuc system for verifying targeting of the predicted EspZ TM regions to the membrane and for assessing the role of the GXXXG sequences in EspZ dimerization/oligomerization. Directional targeting of the TM region to the inner membrane allows the periplasmic MBP domain to complement the growth of the ΔmalE strain in medium containing maltose as the sole carbon source. In contrast to an 'empty' vector control, constructs containing EPEC EspZ TM1, or TM2 supported growth of the ΔmalE strain on broth containing maltose, confirming membrane localization of the respective EspZ domains. TM domain interactions induce dimerization of cytoplasmic ToxR domains, allowing the transcriptional activator to bind to the ctx promoter and promote expression of the downstream luciferase reporter. The TM domains from glycophorin A (GpA) and neuropilin-1 (NRP1), known to homodimerize via GXXXG interactions, strongly induced luciferase activity in this system. A 17-residue poly-alanine stretch (Ala17) was used as a baseline TM control for nonspecific ToxR-dependent luciferase activation. A GpA GXXXG mutant (G831) was impaired for luciferase activation (REF). Constructs expressing EPEC EspZ TM2, but not TM1, induced luciferase expression at levels comparable to, or greater than the positive controls. Mutation of the second and third G residues in the glycine zipper motif (G81L and G85L), but not the first G (G77L), reduced luciferase activity to near-baseline levels. Mutation of all three G residues in the glycine zipper motif also abrogated luciferase expression. This suggests that the TM2 G81XXXG85 of EspZ may facilitate the self-association of EspZ.

FIG. 5B shows the sequences for the EPEC EspZ TM1 (aa35-65, SEQ ID NO: 18) and TM2 (aa74-95. SEQ ID NO: 19) and the other mutant derivatives that were expressed as ToxR-TM-MBP (maltose-binding protein) fusions in an E. coli ΔmalE strain (NT326) for the assay in FIG. 5A: G77L (SEQ ID NO: 20), G81L (SEQ ID NO: 21), G83L (SEQ ID NO: 22), and Triple (SEQ ID NO: 23).

thus, mice infected with ΔespZ/pespZG83L or ΔespZ/pespZG87L displayed reduced mortality compared to the WT-complemented mutant strains.

Figure 8A:
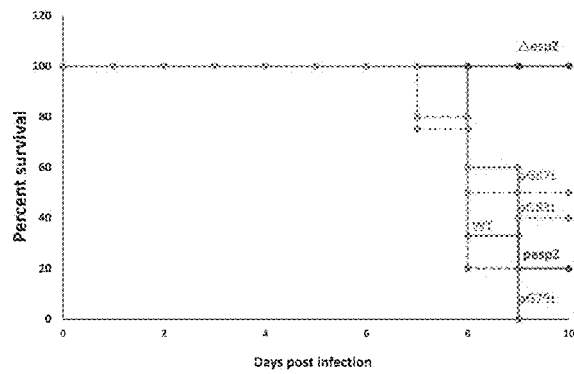
FIG. 8A shows comparisons of survival of C3H/HeJ mice with various ΔespZ strains complemented with plasmids encoding either wild type (WT) or site-directed mutants specific for the glycine zipper region of EspZ. ΔespZ failed to cause mortality in the C3H/HeJ mice, while complementation of the mutant with pespZWT or pespZG79L restored the ability to induce a high level of lethality. Complementation with pespZG83L or pespZG87L, on the other hand, partially complemented the C. rodentium ΔespZ defect.
Figure 8B:
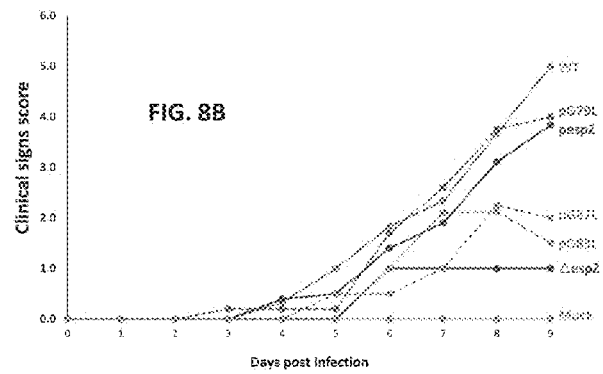

FIG. 8B shows comparisons of clinical symptoms of C3H/HeJ mice with various ΔespZ strains complemented with plasmids encoding either wild type (WT) or site-directed mutants specific for the glycine zipper region of EspZ. ΔespZ failed to cause disease in the C3H/HeJ mice, while complementation of the mutant with pespZWT or pespZG79L restored the ability to induce clinical symptoms. Complementation with pespZG83L or pespZG87L, on the other hand, partially complemented the *C. rodentium* ΔespZ defect; thus, mice infected with ΔespZ/pespZG83L or ΔespZ/pespZG87L displayed moderate clinical signs compared to the WT-complemented mutant strains.

Figure 9A:
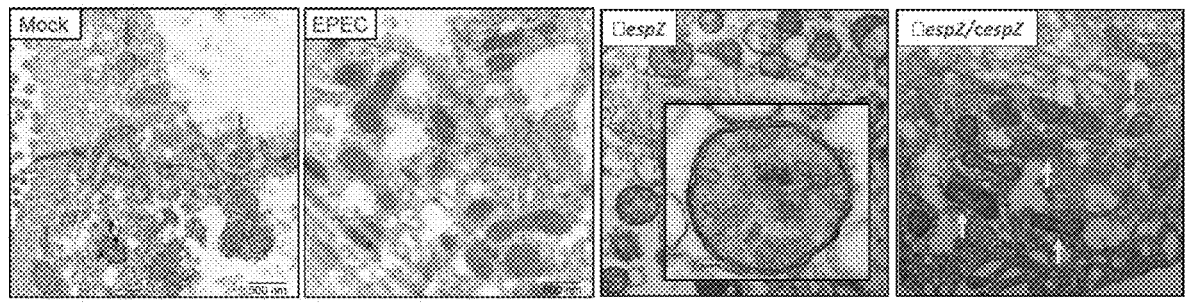

FIG. 9A shows transmission electron microscopy of wild type (WT) EPEC-infected host cells (middle left panel) and mock-infected cells (left panel), revealing elongated mitochondria in EPEC-infected host cells. Cells infected with ΔespZ (middle right panel) had fragmented swollen mitochondria, often enclosed in a double membrane, suggestive of mitophagy. Complementation (right panel) reversed the phenotype. The inset in the middle right panel is a double-membraned organelle. Note 3 hour infection; MOI=100; Caco-2 BBe cells.

Figure 9B:
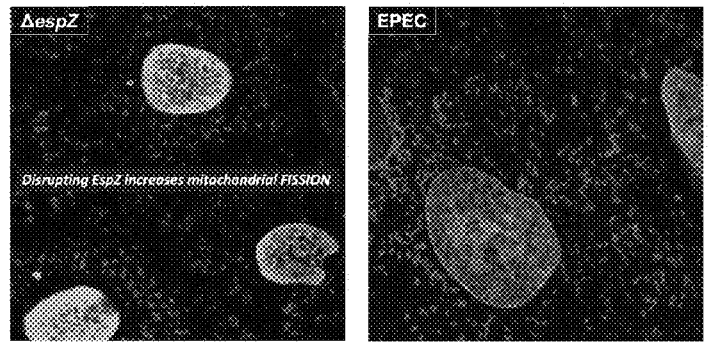

FIG. 9B shows immunofluorescence microscopy of EPEC-infected host cells (right panel) and ΔespZ infected cells (left panel), showing that disrupting EspZ increases mitochondrial fission. Red=COXIV (mitochondrial stain); blue=DAPI stain. Note 3 hour infection; MOI=100; Caco-2 BBe cells.

Figure 10:
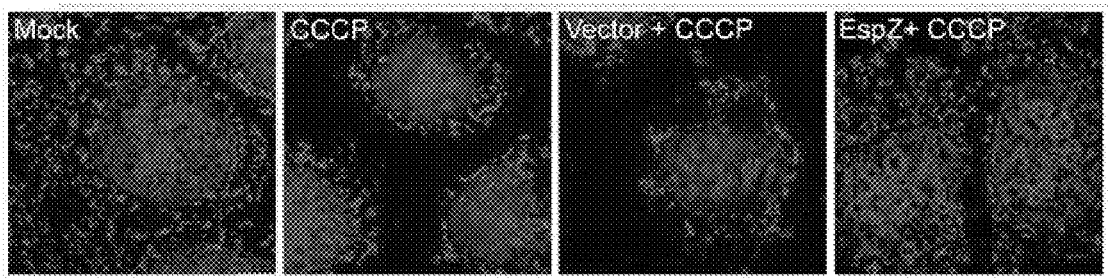

FIG. 10 shows CCCP treatment causes fragmentation of the mitochondrial network and its retraction towards the nucleus (compared to mock-treated controls). In transfected cells, EspZ prevented COOP-induced perturbation of the mitochondrial network (compared to control vector-transfected cells). Red=COXIV (mitochondrial stain); blue=DAPI stain.

Figure 11:
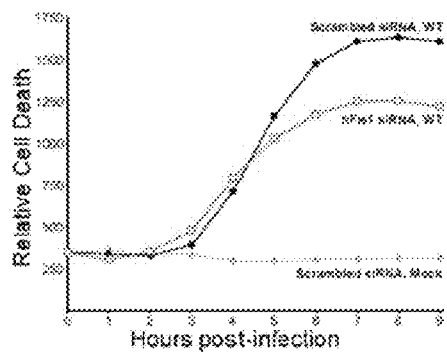

FIG. 11 shows siRNA-mediated hFis1 (a mitochondrial protein) depletion mitigates EPEC-induced host cell death.

Figure 12:
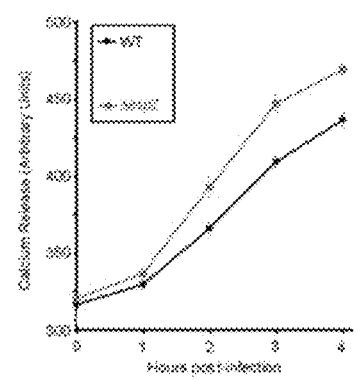

FIG. 12 shows that host cells infected with ΔespZ resulted in a more robust calcium release, indicating EspZ prevents calcium release from host cells.

DETAILED DESCRIPTION OF THE INVENTION

I. Assessment of Essential Regions of EspZ

To preliminarily define the EspZ residues essential for its cytoprotective function, targeted mutations were introduced into pSR6 to systematically replace ~5 amino acid segments with alanine residues (except in M6, M7, M12 and M13, where the glycines were replaced with valine residues). The N-terminal 20 amino acid type III secretion signal was not included in the analysis. 16 mutant constructs were generated (see FIG. 1).

The corresponding plasmids were transformed into ΔespZ and assessed for complementation of the cell death phenotype using propidium iodide uptake studies. Ten mutant constructs showed minimal defects in complementation relative to pSR6 for curtailing host cell death, while three mutants (M6, M10 and M11) were modestly impaired for this phenotype (see FIG. 2). Three mutants, M4, M12, and M13, were significantly defective in their ability to complement ΔespZ (see FIG. 2).

Impaired secretion/translocation of the mutated protein could underlie the complementation defect. To address this possibility, the corresponding constructs were cloned into a eukaryotic vector, and transfected into C2BBe cells. As was reported previously, transfected host cells expressing WT EspZ were protected from ΔespZ-infection induced death, compared to vector-transfected cells. Cells expressing EspZM4, but not EspZM12 or EspZM13, were similarly protected from ΔespZ-induced cell death (data not shown). Thus, the region of EspZ spanning amino acids 74-85 may be essential for its ability to promote the survival of EPEC-infected intestinal epithelial cells.

The TM2 region spanning 74-85 includes a putative 'glycine-zipper' motif (G77XXXG81XXXG85). Transmembrane GXXXG motifs can facilitate helix packaging, and mediate homo- and heterotypic interactions of various membrane-associated proteins. Site-directed mutagens were engineered to individually replace the G residues within the EPEC EspZ glycine zipper motif, respectively, with hydrophobic, but bulkier leucine residues (G77L, G811_, G85L). The constructs were transformed into EPEC ΔespZ. In assays monitoring host cell death (see FIG. 3), alteration of the first two G residues of the glycine zipper (G77L, G81L) resulted in a failure to complement EPEC ΔespZ; mutation of the third G residue, on the other hand, had minimal impact on EspZ function in the cytoprotection assay. This helps show that sequences within a glycine zipper sequence may be essential for the cytoprotective effects of EspZ on infected host cells.

A TEM-1 β-lactamase reporter system was used to monitor effector translocation into infected cells. As shown in FIG. 4, compared to uninfected cells, WT EPEC infection resulted in a progressive increase in the TEM-1 β-lactamase-dependent breakdown (detected via a fluorescence shift) of the substrate CCF2. ΔespZ infection resulted in significantly greater effector translocation, and this was reversed by low-copy-plasmid complementation, consistent with a role for EspZ in limiting effector translocation. Site-specific alteration of the three G residues in the glycine zipper motif variably impacted the rheostat function of EspZ; G to L mutation of the last G residue (G85) had minimal impact on rheostat function, while alteration of the first and second G residues (G77 and G83) partially impaired function.

Membrane-localized GXXXG sequences can promote homo- and hetero-typic interactions between proteins. Referring to FIG. 5A and FIG. 5B, a ToxLuc system was used to verify targeting of the predicted EspZ TM regions to the membrane and to assess the role of GXXXG sequences in EspZ dimerization/oligomerization. EPEC EspZ TM1 (aa35-65) and TM2 (aa74-95), and various mutant derivatives were expressed as ToxR-TM-MBP (maltose-binding protein) fusions in an *E. coil* ΔmalE strain (NT326). Western blot analyses confirmed robust expression of all ToxR-TM-MBP fusion proteins. Directional targeting of the TM region to the inner membrane allows the periplasmic MBP domain to complement the growth of the ΔmalE strain in medium containing maltose as the sole carbon source. In contrast to an 'empty' vector control, constructs containing EPEC EspZ TM1, TM2, or *C. rodentium* TM2 supported growth of the ΔmalE strain on broth containing maltose, confirming membrane localization of the respective EspZ domains. TM domain interactions induce dimerization of cytoplasmic ToxR domains, allowing the transcriptional activator to bind to the ctx promoter and promote expression of the downstream luciferase reporter. The TM domains from glycophorin A (GpA) and neuropilin-1 (NRP1), known to homodimerize via GXXXG interactions, strongly induced luciferase activity in this system. A 17-residue poly-alanine stretch (Ala17) was used as a baseline TM control for nonspecific ToxR-dependent luciferase activation. As noted previously, a GpA GXXXG mutant (G83I) was impaired for luciferase activation (REF). Constructs expressing EPEC EspZ TM2, but not TM1, induced luciferase expression at levels comparable to, or greater than the positive controls. Mutation of the second and third G residues in the glycine zipper motif (G81L and G85L), but not the first G (G77L), reduced luciferase activity to near-baseline levels. Mutation of all three G residues in the glycine zipper motif also abrogated luciferase expression. This suggests that EspZ self-associates within the membrane, and this is facilitated by the TM2 G81XXXG85.

Figure 6:
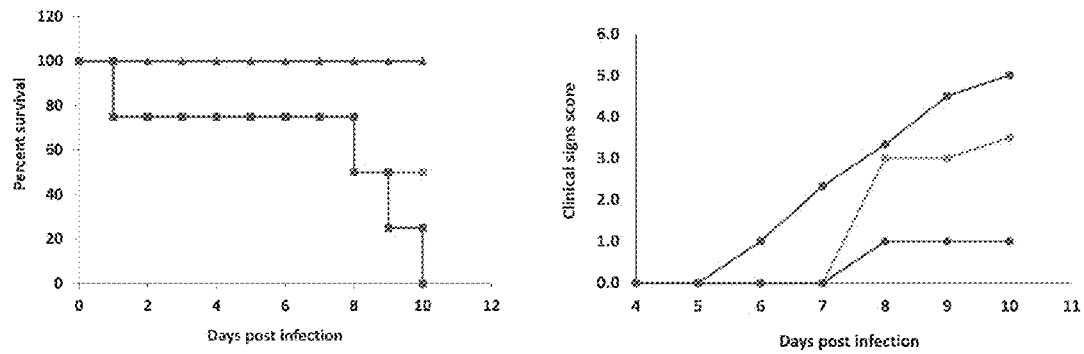
FIG. 6 shows the results of in vivo testing of ΔespZ, ΔespZ/pespZ, and C. rodentium in C3H/HeJ mice. Isogenic WT, ΔespZ and ΔespZ/pespZ strains initially colonized the mouse intestine robustly, exhibiting comparable fecal bacterial loads on day 2 post-infection (see bottom panel). C. rodentium WT (a murine NE pathogen) and ΔespZ/pespZ strains induced robust clinical symptoms, and most infected animals succumbed by day-10 post-infection (WT=50% lethality; ΔespZ/pespZ 100% mortality), consistent with a previous report. Mock- and ΔespZ-infected animals induced little to no symptoms, and all animals survived the duration of the infection (top left panel=survival; top right panel=symptoms. Bacterial burden in the stool was high and consistently maintained for WT- and ΔespZ/pespZ-infected animals, and rapidly decreased for ΔespZ-infected animals after Day 8 (bottom panel).

A C3H/HeJ mouse model was used to assess the contribution to virulence of EspZ and of the residues within the glycine zipper motif. In the experiment, isogenic WT, ΔespZ and ΔespZ/pespZ strains initially colonized the mouse intestine robustly, exhibiting comparable fecal bacterial loads on day 2 post-infection (FIG. 6, bottom panel). C. rodentium WT (a murine NE pathogen) and ΔespZ/pespZ strains induced robust clinical symptoms, and most infected animals succumbed by day-10 post-infection (WT=50% lethality; ΔespZ/pespZ=100% mortality), consistent with a previous report. Mock- and ΔespZ-infected animals induced little to no symptoms, and all animals survived the duration of the infection (see FIG. 6, top left panel and top right panel). Bacterial burden in the stool was high and consistently maintained for WT- and ΔespZ/pespZ-infected animals, and rapidly decreased for ΔespZ-infected animals after Day 8 (see FIG. 6, bottom panel).

Figure 7:
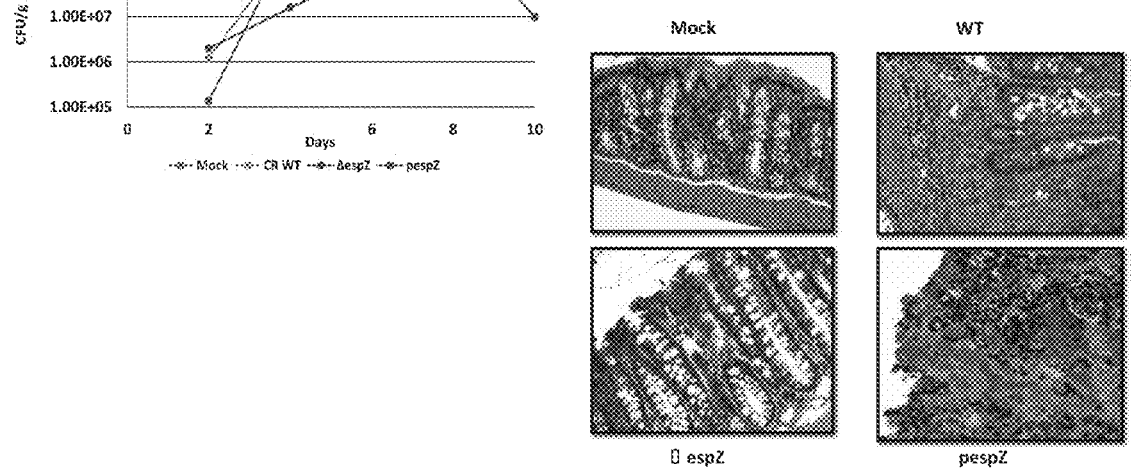
FIG. 7 shows H&E staining of colon samples at day 8-post infection, showing heavy colonization in WT-infected animals (top right panel) and ΔespZ/pespZ-infected animals (bottom right panel) compared to mock infected animals (top left panel). WT-infected animals (top right panel) and ΔespZ/pespZ-infected animals (bottom right panel) also exhibited enlarged intestinal crypts, reduced goblet cells number, extensive tissue damage with ulceration and necrosis in the lumen, and profound neutrophil infiltration. In sharp contrast, colons from ΔespZ-infected animals (bottom left panel) were intact, with well-formed stool pellets and little or no evidence of inflammation or intestinal pathology. This suggests EspZ is essential for NE pathogen virulence.

Referring to FIG. 7, H&E staining of the colon at day-8 p.i. showed heavy colonization in WT- and ΔespZ/pespZ-infected animals. WT and ΔespZ/pespZ-infected animals also exhibited enlarged intestinal crypts, reduced goblet cells number, extensive tissue damage with ulceration and necrosis in the lumen, and profound neutrophil infiltration. In sharp contrast, colons from ΔespZ-infected animals were intact, with well-formed stool pellets and little or no evidence of inflammation or intestinal pathology.

To assess a role for the glycine zipper motif in EspZ function in vivo, C3H/HeJ mice were infected with ΔespZ strains complemented with plasmids encoding either WT or site-directed mutants specific for the glycine zipper region. Consistent with the observations in FIG. 6, ΔespZ failed to cause disease or mortality in the C3H/HeJ mice, while complementation of the mutant with pespZWT or pespZG79L restored the ability to induce clinical symptoms and high level of lethality (see FIG. 8A, FIG. 8B). Complementation with pespZG83L or pespZG87L, on the other hand, partially complemented the C. rodentium ΔespZ defect; thus, mice infected with ΔespZ/pespZG83L or ΔespZ/pespZG87L displayed moderate clinical signs and reduced mortality comparted to the WT-complemented mutant strains. Together with the data presented above, this suggests a correlation between the ability of EspZ to self-associate and promote disease and lethality in an animal model of NE infection.

Referring to FIG. 9A, transmission electron microscopy of WT EPEC-infected host cells (compared to mock-infected cells) revealed elongated mitochondria. Cells infected with ΔespZ, had fragmented swollen mitochondria, often enclosed in a double membrane, suggestive of mitophagy. This was also visualized using immunofluorescence microscopy (see FIG. 9B). Complementation reversed the phenotype.

The uncoupler carbonyl cyanide m-chlorophenylhydrazone (COOP) induces Fis1- and Drp1-dependent mitochondrial fission. In transfected cells, EspZ prevented COOP-induced perturbation of the mitochondrial network (see FIG. 10). Thus, EspZ may be necessary and sufficient for inhibiting mitochondrial fission.

In a split-ubiquitin two-hybrid assay, the mitochondrial protein hFis1 was identified as a putative EPEC EspZ partner. Interaction was confirmed via immuno-precipitation (not shown). hFis1 regulates mitochondrial fission, and integrates the ER/mitochondrial stress axis; its overexpression results in cell death56. siRNA-mediated hFis1 ablation protected epithelial cells from EPEC-induced death (see FIG. 11).

Referring to FIG. 12, infection of host cells with ΔespZ resulted in more robust $Ca^{2+}$ release. EPEC-induced cell death is not inhibitable by caspase inhibitors and is reminiscent of mitochondrial $Ca^{2+}$ overload necroptosis; in a siRNA screen, depletion of the mitochondrial $Ca^{2+}$ importer VDAC1 made cells less susceptible to EPEC-induced death (not shown).

II. Methods and Compositions for Inhibiting EspZ

The present invention features methods, systems, and compositions (e.g., inhibitor peptides) for inhibiting EspZ function (or for inhibiting function of an EspZ equivalent). The methods, systems, and compositions herein may help reduce the virulence of pathogens that utilize EspZ or EspZ equivalent, such as those pathogens that belong to the attaching-effacing (A/E) family.

The compositions of the present invention for inactivating EspZ or an EspZ equivalent may comprise inhibitor peptides. The inhibitor peptides may target one or more regions of EspZ or an EspZ equivalent. In certain embodiments, the inhibitor peptide binds to or interacts with EspZ (or an EspZ equivalent) such that EspZ (or an EspZ equivalent) cannot function properly, e.g., the inhibitor peptides may reduce or block the ability of EspZ (or an EspZ equivalent) to function (e.g., reduce of block the ability of EspZ/EspZ equivalent to allow for colonization, reduce or block the ability of EspZ/EspZ equivalent to inhibit apoptosis, etc.).

The inhibitor peptide may target a region (a susceptibility region), e.g., a particular group of amino acids, of the EspZ or the EspZ equivalent protein. For reference, the sequence of EspZ is as follows: MEAANLSPSGAVLPLAATIN GNNPVDEKTGVMQSEGGTSRSVRILGGVLIGAGV-LAAIGTGIAAMCVDDPSQRLGL GIAAGVLGGVTTVAGGLAMKYA (SEQ ID NO: 1).

As an example, the inhibitor peptide may target one or more of amino acids 37-42 of EspZ. In certain embodiments, the inhibitor peptide may target one or more of amino acids 33-56 of EspZ. In certain embodiments, the inhibitor peptide may target one or more of amino acids 36-52 of EspZ. In certain embodiments, the inhibitor peptide may target one or more of amino acids 25-60 of EspZ. In certain embodiments, the inhibitor peptide may target one or more of amino acids 20-75 of EspZ. In certain embodiments, the inhibitor peptide may target one or more of amino acids 1-75 of EspZ. In certain embodiments, the inhibitor peptide may target one or more of amino acids 75-98 of EspZ. In certain embodiments, the inhibitor peptide may target one or more of amino acids 75-85 of EspZ. In certain embodiments, the inhibitor peptide may target one or more of amino acids 71-89 of EspZ. In certain embodiments, the inhibitor peptide may target one or more of amino acids 60-98 of EspZ. In certain embodiments, the inhibitor peptide may target one or more of amino acids 70-98 of EspZ. In certain embodiments, the inhibitor peptide may target one or more of amino acids 60-85 of EspZ. In certain embodiments, the inhibitor peptide may target one or more of amino acids 72-94 of EspZ.

In certain embodiments, the inhibitor peptides target one or both of the transmembrane (TM) domains, e.g., TM1 or a portion thereof, TM2 or a portion thereof, or both TM1 and TM2 (or portions thereof). In certain embodiments, the inhibitor peptides bind to one or both of the TM domains (or a portion thereof) and prevent dimerization and/or oligomerization of EspZ.

In certain embodiments, the inhibitor peptide comprises a targeting peptide (the portion of the inhibitor peptide that targets EspZ) linked to (directly or indirectly to the N-terminus or C-terminus) a cell-penetrating peptide (CPP) for enhancing penetration of the inhibitor peptide (the targeting peptide) into a cell. Non-limiting examples of cell-penetrating peptides (CPPs) include HIV-1 Tat$_{48-60}$ (GRKKRRQRRRPPQ, SEQ ID NO: 24), HIV-1 Tat$_{49-57}$ (RKKRRQRRR, SEQ ID NO: 25), Penetratin (pAntp$_{43-58}$) (RQIKIWFQNRRMKWKK, SEQ ID NO: 26), Polyarginines, DPV1047 (VKRGLKLRHVRPRVTRMDV, SEQ ID NO: 27), MPG (GALFLGFLGAAGSTMGAWSQPKKKRKV, SEQ ID NO: 28), Pep-1 (KETWWETWWTEWSQPKKKRKV, SEQ ID NO: 29), pVEC (LLIILRRRIRKQAHAHSK, SEQ ID NO: 30), ARF (1-22) (MVRRFLVTLRIRRACGPPRVRV, SEQ ID NO: 31), BPrPr(1-28) (MVKSKIGSWILVLFVAMWSDVGLCKKRP, SEQ ID NO: 32), MAP (KLALKLALKALKAALKLA, SEQ ID NO: 33), Transportan (GWTLNSAGYLLGKINLKALAALAKKIL, SEQ ID NO: 34), p28 (LSTAADMQGVVTDGMASGLDKDYLKPDD, SEQ ID NO: 35), VT5 (DPKGDPKGVTVTVTVTVTGKGDPKPD, SEQ ID NO: 36), Bac 7 (Bac$_{1-24}$) (RRIRPRPPRLPRPRPRPLPFPRPG, SEQ ID NO: 37), C105Y CSIPPEVKFNKPFVYLI, SEQ ID NO: 38), PFVYLI (PFVYLI, SEQ ID NO: XXXXX), Pep-7 (SDLWEMMMVSLACQY, SEQ ID NO: 39), and PTD-4 (YARAAARQARA, SEQ ID NO: 40). See also Dietz and Bahr 2004, Molecular and Cellular Neuroscience 27:85-131, Beerens et al., 2003, Curr Gene Ther. 3(5):486-94, and Biller et al., 2009, Clinical Cancer Research 15:100-109, the disclosures of which are incorporated herein in their entirety. Cell-penetrating peptides are II known to one of ordinary skill in the art.

In some embodiments, the targeting peptide is directly or indirectly connected to the CPP. In some embodiments, the CPP is N-terminal to the targeting peptide. In some embodiments, the targeting peptide is N-terminal to the CPP. In some embodiments, the targeting peptide is connected to the CPP by a linker. Linkers are well known to one of ordinary skill in the art. In some embodiments, the linker is a peptide linker. In some embodiments, there is no linker (e.g., the linker is 0 amino acids in length). In some embodiments, the linker is 1-5 amino acids in length. In some embodiments, the linker is 1-10 amino acids in length. In some embodiments, the linker is 1-15 amino acids in length. In some embodiments, the linker is 1-20 amino acids in length. In some embodiments, the linker is 1-25 amino acids in length. In some embodiments, the linker more than 25 amino acids in length.

In certain embodiments, the targeting peptide of the inhibitor peptide (the portion of the inhibitor peptide that targets EspZ) is related to a portion of the sequence of EspZ, e.g., the targeting peptide may have a sequence that is related to one of the transmembrane domains (or a portion thereof) of EspZ. For example, FIG. 5B shows several examples of sequences related to the transmembrane 2 (TM) region of EspZ.

Table 1 below lists several non-limiting examples of targeting peptides of inhibitor peptides (without the cell-penetrating peptide portion). SEQ ID NO: 20, SEQ ID NO: 21, SEQ ID NO: 22, and SEQ ID NO: 23 are also shown in Table 1. The present invention is not limited to the examples listed in Table 1. For example, in certain embodiments, the inhibitor peptide is a truncated version of one of the peptides in Table 1. In certain embodiments, the inhibitor peptide comprises one of the peptides in Table 1 with one or more additional amino acids. In certain embodiments, the inhibitor peptide comprises one of the peptides in Table 1 with one or more additional amino acids or amino acid segments from EspZ.

TABLE 1

| SEQ ID NO: | Name | Sequence |
|---|---|---|
| 20 | G77L | LGLLIAAGVLGGVTTVAGGLAMK |
| 21 | G81L | LGLGIAALVLGGVTTVAGGLAMK |
| 22 | G83L | LGLGIAAGVLGLVTTVAGGLAMK |
| 23 | Triple | LGLLIAALVLGLVTTVAGGLAMK |
| 41 | G77L-2 | LGLLIAAGVLGGVTTVAG |
| 42 | G77L-3 | LGLLIAAGVLGGVT |
| 43 | G77L-4 | LGLLIAAGVIGGVTTVAG |
| 44 | G77L-5 | LGLLFAAGVLGGVTTVAG |
| 45 | G77L-6 | LGLLIAAGVLGGVSTVAG |
| 46 | G77L-7 | LGLLIAAGVLGFVTTVAG |
| 47 | G77L-8 | LGLLIAAGLLGGVTTVAG |
| 48 | G81L-2 | LGLGIAALVLGGVTTVAG |
| 49 | G81L-3 | LGLGIAALVLGGVT |
| 50 | G81L-4 | LGLGIAALVLNGVTTVAG |
| 51 | G81L-5 | LGLGIAALVLAGVTTVAG |
| 52 | G81L-6 | LGLGIAALVLGGVSTVAG |
| 53 | G81L-7 | LGLGIAALVLGGVTTLAG |
| 54 | G81L-8 | LGLGIAALLLGGVTTVAG |
| 55 | G83L-2 | LGLGIAAGVLGLVTTVAG |
| 56 | G83L-3 | LGLGIAAGVLGLVT |
| 57 | G83L-3 | LGLGIAAGVLGLVTTLAG |
| 58 | G83L-3 | LGLGIAAGVLPLVTTVAG |
| 59 | G83L-3 | LGLGIAAAVLGLVTTVAG |
| 60 | G83L-3 | LGLGIAAGVLGLLTTVAG |
| 61 | G83L-3 | LGLGIAAGVLGLVTSVAG |
| 62 | Triple-2 | LGLLIAALVLGLVTTVAG |
| 63 | Triple-3 | LGLLIAALVLGLVT |
| 64 | Triple-3 | LGLLIAALVLGLVTTLAG |
| 65 | Triple-3 | LGLLIAALVLPLVTTVAG |
| 66 | Triple-3 | LGLLIAALVLALVTTVAG |

TABLE 1-continued

| SEQ ID NO: | Name | Sequence |
|---|---|---|
| 67 | Triple-3 | LGLLIAALVLGLLTTVAG |
| 68 | Triple-3 | LGLLIAALVLGLVSTVAG |

In some embodiments, the targeting peptide is between 5 to 10 amino acids in length. In some embodiments, the targeting peptide is between 5 to 15 amino acids in length. In some embodiments, the targeting peptide is between 5 to 20 amino acids in length. In some embodiments, the targeting peptide is between 5 to 30 amino acids in length. In some embodiments, the targeting peptide is between 10 to 20 amino acids in length. In some embodiments, the targeting peptide is between 10 to 30 amino acids in length. In some embodiments, the targeting peptide is between 15 to 30 amino acids in length. In some embodiments, the targeting peptide is between 15 to 40 amino acids in length. In some embodiments, the targeting peptide is between 15 to 50 amino acids in length. In some embodiments, the targeting peptide is between 20 to 30 amino acids in length. In some embodiments, the targeting peptide is between 20 to 50 amino acids in length. In some embodiments, the targeting peptide is 5 amino acids in length. In some embodiments, the targeting peptide is 6 amino acids in length. In some embodiments, the targeting peptide is 7 amino acids in length. In some embodiments, the targeting peptide is 8 amino acids in length. In some embodiments, the targeting peptide is 9 amino acids in length. In some embodiments, the targeting peptide is 10 amino acids in length. In some embodiments, the targeting peptide is 11 amino acids in length. In some embodiments, the targeting peptide is 12 amino acids in length. In some embodiments, the targeting peptide is 13 amino acids in length. In some embodiments, the targeting peptide is 14 amino acids in length. In some embodiments, the targeting peptide is 15 amino acids in length. In some embodiments, the targeting peptide is 16 amino acids in length. In some embodiments, the targeting peptide is 17 amino acids in length. In some embodiments, the targeting peptide is 18 amino acids in length. In some embodiments, the targeting peptide is 19 amino acids in length. In some embodiments, the targeting peptide is 20 amino acids in length. In some embodiments, the targeting peptide is 21 amino acids in length. In some embodiments, the targeting peptide is 22 amino acids in length. In some embodiments, the targeting peptide is 23 amino acids in length. In some embodiments, the targeting peptide is 24 amino acids in length. In some embodiments, the targeting peptide is 25 amino acids in length. In some embodiments, the targeting peptide is 26 amino acids in length. In some embodiments, the targeting peptide is 27 amino acids in length. In some embodiments, the targeting peptide is 28 amino acids in length. In some embodiments, the targeting peptide is 29 amino acids in length. In some embodiments, the targeting peptide is 30 amino acids in length. In some embodiments, the targeting peptide is more than 30 amino acids in length. In some embodiments, the targeting peptide is from 30 to 40 amino acids in length. In some embodiments, the targeting peptide is from 40 to 50 amino acids in length. In some embodiments, the targeting peptide is from 50 to 80 amino acids in length. In some embodiments, the targeting peptide is from 50 to 100 amino acids in length.

Inhibitor peptides and/or cell-penetrating peptides may be synthesized by a commercial or research entity, e.g., Creative Peptides, Shirley, N.Y., USA, etc.

The present invention also features methods for synthesizing inhibitor peptides for targeting EspZ and inhibiting or reducing virulence, colonization, dimerization, downstream signaling effects, etc. The present invention also features methods for screening inhibitor peptides for determining effectiveness of targeting EspZ and inhibiting or reducing virulence, colonization, dimerization, downstream signaling effects, etc.

The present invention also features methods for inhibiting or reducing virulence of a pathogen of the attaching-effacing (A/E) family (e.g., E. coil). The method may comprise introducing to the pathogen an inhibitor peptide according to the present invention (e.g., an inhibitor peptide for targeting EspZ, for disrupting EspZ function, for inhibiting dimerization, for inhibiting downstream signaling, effects, etc.), wherein the inhibitor peptide disrupts EspZ function to inhibit or reduce virulence of the pathogen.

The present invention also features methods for inhibiting or reducing colonization of a pathogen of the attaching-effacing (NE) family (e.g., E. coil). In some embodiments, the method comprises introducing to the pathogen an inhibitor peptide according to the present invention, wherein the inhibitor peptide disrupts EspZ function to inhibit or reduce colonization of the pathogen.

The present invention also features methods for treating a subject (in need thereof) infected with a pathogen in the attaching-effacing (NE) family (e.g., E. coli). In some embodiments, the method comprises introducing to the subject an inhibitor peptide according to the present invention, wherein the inhibitor peptide disrupts EspZ function to inhibit or reduce virulence of the pathogen.

EXAMPLE 1

Targeting EspZ $G^{81}XXXG^{85}$

A transmembrane (TM) GXXXG sequence that is critical for EspZ function in vitro (and is required for causing disease-symptoms in vivo) has been identified. The GXXXG motif is present in diverse proteins and promotes protein-protein interactions. Consistent with this, EspZ self-associates in the membrane, and this is abrogated by disruption of the GXXXG motif ($G^{81} \rightarrow L$ or $G^{85} \rightarrow L$). The corresponding mutants are also impaired for supporting virulence in animal models. Notably, the $G^{8} \rightarrow L$ mutation blocked all known EspZ functions, and was the most impaired for promoting virulence.

Inhibitor peptides as described herein may be designed to target against EspZ $G^{81}XXXG^{85}$ to block EspZ activity, as well as its self-association, and thereby mitigate virulence and disease. Strategies for targeting EspZ $G^{81}XXXG^{85}$ include but are not limited to biased peptides and small molecule inhibitors. Biased peptides may be peptide mimetics of the EspZ TM2 region, including $G^{81}XXXG^{85}$, or derivatives thereof. The peptide mimetics may block EspZ self-association and curtail EPEC- and EHEC-human disease. Specific inhibitory peptides may be rationally designed using available computational resources (e.g., CHAMP, Yin 1997). A high-throughput screen may be used to identify small molecules from publicly-available libraries that inhibit EspZ-EspZ interactions; both FDA-approved libraries (for repurposing existing drugs) as well as larger resource-containing libraries may be used.

Screens may assess interference of EspZ self-association, e.g., using the ToxLuc assay (Bronniman, 2013). Further, the ability of select inhibitory molecules to block EspZ-dependent host cell protection in vitro and/or their toxicity to eukaryotic cells may be assessed. Molecules may also be assessed for their ability to block A/E pathogen virulence in vivo.

EXAMPLE 2

Screening Inhibitor Peptides

The effectiveness of the inhibitory peptides to block EspZ function may be assessed using two complementary screening assays (1) Host cell death assay: Epithelial cells will be infected with EPEC or a ΔespZ mutant in the presence of the specific peptides, or media alone. EspZ-specific inhibitors will induce greater cell death of EPEC-infected cells, but not ΔespZ-infected cells, relative to media alone. (2) Dimerization inhibition assay: EspZ self-association leads to luciferase expression in the ToxLuc system (FIG. 5A). The same assays may be performed in the presence of the specific peptides: molecules that inhibit EspZ dimerization will decrease luciferase production.

The disclosures of the following U.S. Patents are incorporated in their entirety by reference herein: U.S. Pat. App. No. 2010/0291596; U.S. Pat. App. No. 2010/0222261.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting or" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An inhibitor peptide for inactivation of EspZ, said inhibitor peptide comprising:
   a) a targeting peptide, the targeting peptide binds to or interacts with at least a portion of EspZ, wherein the targeting peptide comprises one of SEQ ID NOs: 20-23, SEQ ID NOs: 41-68: and
   b) a cell penetrating peptide (CPP) linked directly or indirectly to the targeting peptide, the CPP is for enhancing penetration of the targeting peptide into a cell:
   wherein the inhibitor peptide disrupts EspZ activity.

2. An inhibitor peptide for inactivation of EspZ, said inhibitor peptide comprising:
   a) a targeting peptide, the targeting peptide binds to or interacts with at least a portion of EspZ, wherein the
   targeting peptide comprises a peptide that is at least 90% identical to one of SEQ ID NOs: 20-23, SEQ ID NOs: 41-68: and
   b) a cell penetrating peptide (CPP) linked directly or indirectly to the targeting peptide, the CPP is for enhancing penetration of the targeting peptide into a cell:
   wherein the inhibitor peptide disrupts EspZ activity.

* * * * *